(12) United States Patent
Giagnorio

(10) Patent No.: US 9,750,681 B2
(45) Date of Patent: Sep. 5, 2017

(54) SKIN CARE COMPOSITION

(75) Inventor: Geralynn Giagnorio, West Chicago, IL (US)

(73) Assignee: JG Skin, Inc., Fort Collins, CO (US)

( * ) Notice: Subject to any disclaimer, the term of this patent is extended or adjusted under 35 U.S.C. 154(b) by 548 days.

(21) Appl. No.: 12/450,596

(22) PCT Filed: Apr. 16, 2008

(86) PCT No.: PCT/US2008/004893
§ 371 (c)(1),
(2), (4) Date: Oct. 1, 2009

(87) PCT Pub. No.: WO2008/133822
PCT Pub. Date: Nov. 6, 2008

(65) Prior Publication Data
US 2010/0047295 A1 Feb. 25, 2010

Related U.S. Application Data

(60) Provisional application No. 60/926,643, filed on Apr. 27, 2007.

(51) Int. Cl.
| A61K 8/97 | (2017.01) |
| A61K 8/06 | (2006.01) |
| A61K 8/55 | (2006.01) |
| A61Q 19/00 | (2006.01) |
| A61K 8/37 | (2006.01) |
| A61K 8/81 | (2006.01) |
| A61Q 1/02 | (2006.01) |
| A61Q 1/04 | (2006.01) |
| A61Q 1/06 | (2006.01) |
| A61Q 1/08 | (2006.01) |
| A61Q 1/10 | (2006.01) |
| A61Q 1/12 | (2006.01) |

(52) U.S. Cl.
CPC .............. *A61K 8/97* (2013.01); *A61K 8/06* (2013.01); *A61K 8/062* (2013.01); *A61K 8/375* (2013.01); *A61K 8/553* (2013.01); *A61K 8/556* (2013.01); *A61K 8/8147* (2013.01); *A61K 8/8152* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61Q 19/00* (2013.01); *A61K 2800/21* (2013.01)

(58) Field of Classification Search
None
See application file for complete search history.

(56) References Cited

U.S. PATENT DOCUMENTS

| 4,797,273 A * | 1/1989 | Linn et al. ........................ 424/59 |
| 6,117,915 A * | 9/2000 | Pereira .................. A61K 8/062 424/59 |
| 6,365,162 B1 * | 4/2002 | Sim .......................... 424/195.17 |
| 2002/0146375 A1 | 10/2002 | Schreiber et al. |
| 2004/0126346 A1 * | 7/2004 | Martin et al. ................... 424/64 |
| 2006/0193921 A1 | 8/2006 | Brown et al. |
| 2006/0204526 A1 | 9/2006 | Lathrop et al. |
| 2007/0003536 A1 | 1/2007 | Zimmerman et al. |

\* cited by examiner

Primary Examiner — Bethany Barham
Assistant Examiner — Barbara Frazier
(74) Attorney, Agent, or Firm — Sunstone IP

(57) ABSTRACT

Skin care emulsion compositions are disclosed comprising an oil-in-water emulsion comprising phospholipid-stabilized, submicron triglyceride particles, botanical material selected from the group consisting of a vegetal material, a marine material and combinations thereof; a polycarboxylate polymer and a phosphate ester-type emulsifier. The skin care compositions can be topically applied to the skin before, and surprisingly, together with, and/or after applying a skin colorant (i.e., pigmented) cosmetic composition to moisturize the skin and achieve, augment, and/or maintain a visibly desirable cosmetic appearance.

19 Claims, No Drawings

SKIN CARE COMPOSITION

CROSS REFERENCE TO RELATED APPLICATIONS

This application is the U.S. National Stage of International Application No. PCT/US/2008/0004893 filed Apr. 16, 2008, which claims benefit of U.S. Provisional Application for Patent Ser. No. 60/926,643 filed Apr. 27,2007, the entire disclosures of which are incorporated herein by reference.

TECHNICAL FIELD OF THE INVENTION

This invention relates to skin care compositions, and more particularly to skin moisturizing compositions for maintaining a desirable visual appearance.

BACKGROUND OF THE INVENTION

Most colorant cosmetic compositions used for beautifying or enhancing the visual appearance of the skin are pigmented and often water-free, such as facial and body make-ups, facial and body powders, eye area cosmetics, lip care products, and the like. Such colorant cosmetics may be applied to selected areas of the skin ranging from spot coverups to larger areas, such as the entire face or body.

However, skin that is exposed to environmental factors, such as sunlight, wind and other weather-related insults, low humidity, household and industrial chemicals, and the like can become dry in texture and appearance. Desiccated skin tends to look weathered, develop unwanted surface lines and small wrinkles, and loses smoothness and softness. When colorant compositions are applied on skin that is not sufficiently moisturized, the desired finished effect may not be visually uniform or pleasing. There is an ongoing need and desire for cosmetically acceptable skin-care compositions that help ameliorate and mitigate the undesirable adverse effects of the environment on skin.

Although many aqueous skin care products are commercially available containing various known moisturizer ingredients, such aqueous skin care products frequently are incompatible with colorant cosmetics that are subsequently applied and adversely diminish or interfere with the visual cosmetic result desired. Cosmeticians, aestheticians, professional makeup artists, and general consumers sometimes attempt to overcome the problem by applying oily, greasy foundation products to the skin before applying the colorant cosmetic or by applying multiple coats of colorant cosmetic. While this approach may result in varying degrees of success, it also increases the risk of irritating the skin, causing comedones, clogging the pores, and the like.

Therefore, there is an ongoing need and desire for a cosmetically acceptable skin-moisturizing product that can be applied to and left on the skin, either before, or after applying a substantially anhydrous colorant cosmetic, without adversely affecting the visual cosmetic appearance desired. The moisturizing skin care composition of this invention fulfills this need.

SUMMARY OF THE INVENTION

Emulsion compositions are disclosed comprising cosmetically acceptable, phospholipid-stabilized, submicron triglyceride particles and botanical materials for topical application to human skin. The compositions are applied to, and left on, the skin of the face and body, and, surprisingly, are compatibly adapted for use either before, together with, or after applying a skin colorant cosmetic.

More particularly, the disclosed skin care emulsion compositions comprise an oil-in-water emulsion comprising phospholipid-stabilized submicron triglyceride particles; a botanical material selected from the group consisting of a vegetal material, a marine material, and combinations thereof; a polycarboxylate polymer, and an effective emulsifying amount of a phosphate ester-type emulsifier.

A particularly preferred oil-in-water emulsion comprises a lecithin-stabilized submicron fatty $C_6$-$C_{10}$ triglyceride.

A particularly preferred botanical material comprises a combination of a *Hippophae rhamnoides* (sea buckthorn) extract, a *Laminaria digitata* (sea tangle) extract, a *Macrocystis pyrifera* (sea kelp) extract, a *Crithmum maritimum* (sea fennel) extract, an algae extract; and an *Aloe barbadensis* leaf juice.

The polycarboxylate polymer preferably comprises a linear copolymer of acrylic acid capable of forming a water resistant film.

The phosphate ester-type emulsifier preferably is selected from one or more of the following: a $C_8$-$C_{22}$ fatty alcohol phosphate monoester, a $C_8$-$C_{22}$ fatty alcohol phosphate diester, a $C_2$-$C_4$ alkoxylated $C_8$-$C_{22}$ fatty alcohol phosphate mono ester, a $C_2$-$C_4$ alkoxylated $C_8$-$C_{22}$ fatty alcohol phosphate diester, a salt of any of the foregoing, and a combination of two or more of the foregoing emulsifiers.

In one aspect, the skin care composition can be topically applied to the skin and left thereon to moisturize, smooth, and soothe the skin in a skin care regimen to mitigate and ameliorate the undesirable adverse effects of the environment and to maintain a desirable smooth, soft, visual appearance.

In another aspect, the skin care composition can be incorporated into all or a part of a skin-beautifying cosmetic procedure to augment and/or maintain a desired cosmetic effect. For example, the skin care composition can be topically applied to the skin as a moisturizing foundation before applying a colorant cosmetic thereto without adversely affecting the subsequent visual cosmetic result desired. Alternatively, a sufficient amount of the skin care composition can be admixed with a colorant cosmetic of choice to provide a more flowable or spreadable pigmented cosmetic, and the admixture then applied to the skin to achieve a desired cosmetic appearance. In yet another alternative, after a colorant cosmetic has been applied, the skin care composition can be topically applied to the same skin area over the applied colorant cosmetic to help maintain a long-lasting cosmetic effect without adversely affecting the desired appearance of the cosmetic result. Surprisingly, the skin care composition can be admixed with a substantially anhydrous colorant cosmetic to provide a substantially flowable or more spreadable pigmented cosmetic to achieve, enhance and/or maintain the cosmetic effect desired.

Also disclosed are kits containing A) a skin care composition of this invention and B) in separately packaged form, at least one colorant cosmetic composition, and preferably C) instructional indicia for admixing compositions A and B for use.

DESCRIPTION OF THE PREFERRED EMBODIMENT

The terms "colorant cosmetic" and "pigmented cosmetic" are used interchangeably herein to refer to cosmetics that are pigment-containing compositions intended for topical use on the face, including the eye area and lips, and the body, including the torso, hands, legs, and feet for the purpose of temporarily imparting a tonal change in the visible appearance of the complexion. Colorant cosmetics, typically include, without limitation, facial makeup, such as foundation, blusher, rouges, concealer, and the like; makeup for the body such as leg makeup, artificial tanning, and the like; powder for the face and body, lip care products, such as lipsticks, lip gloss, and the like; and eye area products, such as mascaras for the eyelashes, eye shadows and eye liners for the eye lids, eye brow products, and the like. The term "skin care" as applied to eye area products includes the eyebrows and eyelashes.

Colorant compositions generally contain a sufficient amount of cosmetically acceptable pigment or pigment blends to impart a detectable tonal effect on the skin. Pigments can include, without being limited thereto, natural and synthetic inorganic pigments, such as carbon black, earth pigments, powdered minerals, titanium dioxide, talcs, mica and the like; natural pigments, such as henna, cochineal, and the like; starches and the like. Colorant compositions preferably contain at least about 5 parts by weight pigment based on the total weight of the composition.

Pigmented compositions can be aqueous or non-aqueous (i.e., substantially anhydrous). Aqueous colorant compositions preferably contain not more than about 55% water, more preferably not more than about 50% water, based on the total weight of the composition. Non-aqueous cosmetics are substantially anhydrous, i.e., water-free, usually in the form of cosmetic solids, such as compressed or loose powders, or semi-solids, such as pastes, gels, sticks and the like or can be flowable liquids. In a non-aqueous cosmetic, water is not an intended ingredient of the formulation. Thus, free water, if any, present in such products, typically is negligible, and in the form of moisture adsorbed by some hygroscopic ingredient or on the surface of the product from exposure to the ambient atmosphere during manufacture or use.

Cosmetic ingredients, additives, products or materials, and optional cosmetic adjuvants, which can be employed in the skin care compositions discussed herein are referred to by their commonly used chemical names or by the international nomenclature commonly referred to as INCI name given them in any edition of the International Cosmetic Ingredient Dictionary and Handbook, (hereafter INCI Dictionary), or in any edition of the CTFA International Buyers' Guide, all published by the Cosmetic, Toiletry, and Fragrance Association, Washington D.C. Numerous commercial suppliers of materials listed by INCI name, trade name, or both, can be found in any edition of the INCI Dictionary and in numerous commercial trade publications, including but not limited to, any edition of the Cosmetic Bench Reference, published by Allured Publishing Corporation, Carol Stream, Ill., and the relevant disclosures of each of the foregoing publications being incorporated herein by reference.

The term "cosmetic adjuvant" includes cosmetically useful product stabilizing and finishing ingredients, well known and conventionally used in the cosmetic arts to maintain the physical stability of a composition, and the visible aesthetic appearance of a composition during storage and during the use of the composition. Cosmetic adjuvants that maintain the stability of products typically include a preservative, a metal-ion chelating agent, an antioxidizing agent, a perfume solubilizer, a pH modifier, a viscosity modifier, and the like, but are not limited thereto. Cosmetic adjuvants that enhance the aesthetics and consumer appeal of the product include, without limitation, a fragrance, a product colorant, and the like.

The disclosed skin care compositions preferably are aqueous emulsions and incorporate therein an oil-in-water emulsion comprising phospholipid-stabilized submicron triglyceride particles; a botanical material selected from the group consisting of a vegetal material, a marine material, and combinations thereof; a polycarboxylate polymer; and a phosphate ester-type emulsifier, as discussed in more detail below. The emulsions can be prepared as oil-in-water, water-in-oil or as multiple emulsions by emulsification techniques generally known in the art. The aqueous skin care compositions are surprisingly compatible with substantially anhydrous cosmetic formulations and can be applied to the skin before, during (together with), or after the application of a substantially anhydrous cosmetic without interfering with the desired visual effect desired.

Oil-in-water emulsions of phospholipid-stabilized submicron triglyceride particles, sometimes called submicron emulsions or nano-emulsions, can be prepared from naturally derived phospholipids, such as soybean lecithin or egg yolk lecithin, or from synthetically prepared phospholipids, such as lecithin derivatives. Triglycerides can be natural (from oils, fats) or synthetic, and include, without limitation thereto, mono-, di-and tri-esters of glycerin and $C_6$-$C_{22}$ fatty acids and mixtures thereof, such as caprylic/capric triglyceride, caprylic/capric/lauric triglyceride, and caprylic/capric/myristic/stearic triglyceride.

A particularly preferred oil-in-water emulsion comprises lecithin-stabilized submicron fatty triglyceride particles having fatty groups with about 6 to about 18 carbon atoms, preferably about 8 to about 10 carbon atoms.

Preferably, the lecithin-stabilized, submicron triglyceride particles also include oil-soluble, auxiliary lipophilic, skin conditioning agents, such as retinyl palmitate, tocopherol acetate, and the like. Cosmetically acceptable, water-soluble solvents, such as alcohols and liquid polyols, are also present in the oil-in-water emulsion. The alcohol is preferably ethanol, and the liquid polyol preferably is a humectant polyhydric alcohol, such as glycerin. The alcohol can also function as a preservative.

Particularly preferred is a transparent, nano-emulsion of oil in water comprising lecithin-stabilized caprylic/capric triglyceride described by the supplier (Mibelle AG-Biochemistry) as having a particle size in the range of about 20 to about 1000 nanometers (nm) in diameter, more preferably in the range of about 30 to about 100 nm in diameter. The lecithin membrane of the particles reportedly is characterized as a unimolecular shell of natural soya phospholipids with a high proportion of phosphatidylcholine that stabilizes the encapsulated oil phase from coalescence in the water phase.

The phospholipid-stabilized submicron triglyceride oil-in-water emulsion preferably is present in the composition in an amount in the range of about 0.001 to about 10 parts by weight, more preferably about 0.005 to about 5 parts by weight, most preferably about 0.1 to about 1 parts by weight, based on the total weight of the skin care composition.

Preferred botanical materials are microbiologically stabilized, water-soluble, concentrated extracts, preferably provided in a liquid form. Particularly preferred are botanical materials provided in a cosmetically acceptable aqueous vehicle, preferably a hydroglycolic vehicle, i.e., containing a polyhydric alcohol such as glycerin, having a physiologically tolerable pH in the range of about pH 4 and about pH 7. Particularly preferred are aqueous extracts of botanical sources rich in minerals and mineral salts, such as *Hippophae rhamnoides*, (sea buckthorn), *Crithmum maritimum* (sea fennel), and brown algae, especially *Laminaria digitata* (sea tangle); *Macrocystis pyrifera* (sea kelp); and botanical sources of bioactive carbohydrates, minerals and moisturizers, such as algae (*Laminaria* and sea weed) and of aloe, especially *aloe barbadensis*.

A particularly preferred botanical material comprises a hydroglycolic extract of a *Hippophae rhamnoides* (sea buckthorn) preferably combined with a hydroglycolic extract of a *Laminaria digitata* (sea tangle); a hydroglycolic extract of *Macrocystis pyrifera* (sea kelp); a hydroglycolic extract of *Crithmum maritimum* (sea fennel); a hydroglycolic extract of an algae, *Aloe barbadensis* leaf juice, and mixtures thereof. "*Aloe barbadensis* leaf juice" is the INCI name for the juice expressed from the leaves of the aloe, *Aloe barbadensis*.

The amount of at least one botanical material present in the composition preferably is in the range of about 0.05 to about 15 parts by weight, more preferably of about 0.25 to about 10 parts by weight, most preferably of about 0.5 to about 5 parts by weight, based on the total weight of the skin care composition. As those skilled in the formulation arts recognize, the actual total amount of botanical material in the composition can vary depending on the concentration of each botanical material present, as selected for achieving the desired topical skin conditioning effect, such as moisturizing, soothing, smoothing, and the like.

The polycarboxylate polymer preferably comprises a copolymer of two or more monomers consisting of acrylic acid, methacrylic acid and a simple ester of acrylic and/or methacrylic acid, given the INCI name Acrylates copolymer. More preferably the polycarboxylate polymer comprises a linear copolymer of acrylic acid capable of forming a water resistant film. Particularly preferred are copolymers of acrylic acid reported as typically containing from 3 to 15 weight percent carboxyl functionality, sold under the trade name AVALURE® AC by Noveon, Inc. The amount of polycarboxylate polymer present preferably is in the range of about 0.05 to about 3 parts by weight, more preferably of about 0.1 to about 2 parts by weight, most preferably of about 0.15 to about 1.5 parts by weight, based on the total weight of the skin care composition.

The skin care composition preferably contains a phosphate ester-type emulsifier ester selected from one or more of the following: a $C_8$-$C_{22}$ fatty alcohol phosphate monoester, a $C_8$-$C_{22}$ fatty alcohol phosphate diester, a $C_2$-$C_4$ alkoxylated $C_8$-$C_{22}$ fatty alcohol phosphate monoester, a $C_2$-$C_4$ alkoxylated $C_8$-$C_{22}$ fatty alcohol phosphate diester, a salt of any of the foregoing, and a combination of two or more of the foregoing emulsifiers. Phosphate esters of $C_{16}$-$C_{18}$ fatty alcohols are preferred. Alkoxylated fatty alcohol phosphate esters preferably have about 2 to about 20 moles of the alkoxylating moieties present for each fatty alcohol moiety, and are preferably either polyethoxylated, polypropoxylated, or both polyethoxylated and polypropoxylated. The phosphoric acid ester-based emulsifiers can be salts of alkali metal hydroxide or organic bases, preferably formed by in situ neutralization. A particularly preferred emulsifier comprises cetyl phosphate, and/or an alkali metal salt thereof. The emulsifier can be present in an amount sufficient to provide a visibly phase-stable emulsion on standing for a period of at least about 24 to about 48 hours storage. The amount of phosphate ester-type emulsifier present in the composition preferably is in the range of about 1 to about 5 parts by weight, more preferably in the range of about 1.5 to about 4.5 parts by weight, based on the total weight of the skin care composition.

The skin care compositions can include auxiliary skin conditioning agents in addition to those provided via the nano-emulsion particles or botanical materials. The term "skin conditioning agents" and grammatical variations thereof as it relates to compositions for skin care includes cosmetically and physiologically tolerable useful lubricious and water-retaining materials, such as humectants, emollients, moisturizers, and the like, well known to those skilled in the cosmetic arts. Non-limiting examples of humectants include polyhydric alcohols, such as glycerin, propylene glycol, butylene glycol, hexylene glycol, sugar alcohols, such as sorbitol, mannitol, galactitol, and the like. Examples of emollients include, without limitation thereto, esters of $C_6$-$C_{22}$ fatty acids, fatty alcohols, and alkoxylated fatty alcohols; silicone fluids (volatile and nonvolatile); silicone copolyols, liquid hydrocarbons, such as mineral oil and the like. Non-limiting examples of moisturizers include organic polyols; salts of hyaluronic acid, lactic acid, and pyrrolidone carboxylic acid; and water soluble polymers, such as polyethylene glycol.

The total amount of auxiliary skin conditioning agents preferably is at least about 10 parts by weight, based on the total weight of the skin care composition. The actual amount of individual or total auxiliary skin conditioning agents present can be readily determined by the skilled formulator based on the effective amount for achieving the desired tactile effect on the skin, without adversely affecting the physical stability of the emulsion composition, or its physiological acceptability.

Other adjuvant ingredients that may be present in the skin care compositions include metal ion chelating agents, (synthetic or natural), such as ethylenediaminetetraacetic acid (EDTA) and salts thereof, citric acid, gluconic acid and salts thereof, such as sodium gluconate, cyclodextrins, phytic acid, carboxylic acids derived from monosaccharides, such as glucaric acid, and the like; cosmetically acceptable preservatives against microbiological deterioration; product colorants, including opacifying and pearlizing materials, such as titanium-coated mica, titanium dioxide, and the like; and fragrance. The adjuvant ingredient need only be present in an amount sufficient to effectively accomplish its respective function. Those skilled in the cosmetic arts recognize that skin conditioning materials may provide more than one of the foregoing benefits or functions.

The final skin care compositions can have a viscosity varying from a pourable liquid, such as a lotion, to a substantially semi-solid, such as a cream or paste, as desired. Particularly preferred is a cream having a physiologically tolerable pH in the range of about pH 5.5 to about pH 7, more preferably in the range of about pH 6 to about pH 6.5 and having a viscosity in the range of about 50,000 to about 150,000 milli-Pascal seconds (mPa·s) measured at a temperature of about 25° C. with a rotating viscometer (Brookfield, RVT with helipath).

The skin care composition of this invention is surprisingly versatile, as it can be topically applied to the skin before, during, and/or after applying a colorant cosmetic to achieve moisturizing effects, and augment and/or maintain longer lasting desirable colorant cosmetic effects. For example, in one preferred method aspect, a skin care composition of this invention can be topically applied to the skin, gently distributed over the skin and left on to moisturize the skin as either part of a skin care regimen or substantially immediately before applying a colorant cosmetic to the same skin site to achieve and maintain the cosmetic effect desired.

In another preferred method aspect, a skin care composition of this invention can be admixed with one or more colorant compositions, using a sufficient amount of each composition to achieve a desirable spreadable consistency and color, and the admixture is topically applied to the skin to concurrently moisturize and beautify the skin. In this aspect, the user can both tailor the visual cosmetic effect as desired and maintain skin moisturization. For example, a colorant powder composition can be admixed with a sufficient amount of skin care composition to achieve a spreadable creamy paste consistency.

In yet another preferred method aspect, a skin care composition of this invention can be applied to a skin site where colorant cosmetic has already been applied, such as over a brow product or lip product or eyelash product or can be applied in multiple applications, to help maintain long-lasting colorant cosmetic effects, moisturize the skin and to achieve novelty effects. Surprisingly, the skin care compositions were particularly compatible with substantially anhydrous pigmented cosmetics and augmented the cosmetic effect achieved.

The moisturizing skin care composition can be preferably provided in kits, with a skin care composition of this invention in packaged form (A), preferably with at least one substantially anhydrous colorant cosmetic composition (B) in separately packaged form and (C) instructional indicia for admixing A and B for use. A preferred kit embodiment also includes one or more of the following implements for performing skin moisturization and skin beautifying; e.g., a sampling scoop or spatula, a mixing spatula, a mixing palette or vessel, disposable gloves, a mirror, and the like. The kit components preferably are contained in an outer package. The outer package can be a box, carton, shrink wrap, bag, or sack, and the like.

Useful instructional indicia can be printed media, aural media, visual aids, electronic media or a combination thereof, which instruct the user on how to admix the kit component (A) with kit component (B) and describe the use of the each component alone or in admixture to achieve the desired cosmetic effects. Printed media includes, but is not limited to, labels attached to or imprinted on the components of the kit, package inserts, pamphlets, books, flyers, and the like. Aural media includes, but is not limited to, tape recordings, audio compact disks, records, and the like. Visual aids include, but are not limited to, photographs, slides, movies, videos, DVDs, and the like. Electronic media includes all forms of electronic data storage media, such as, but not limited to, diskettes, interactive CD-ROMs, interactive DVDs, and the like.

The following examples illustrate the preparation and use of preferred embodiments but are not intended to be limited thereto.

EXAMPLE 1

Materials

For illustration of preferred embodiments, and not by limitation, the following materials identified in the examples are as follows:

Cetearyl alcohol: —INCI name for a mixture of fatty alcohols consisting predominately of cetyl and stearyl alcohol.

Dimethicone—non-volatile silicone (such as Dow Corning 200 Fluid/350 centistokes (cts.).

Cyclopentasiloxane—volatile silicone (such as Dow Corning 245 Fluid).

Nano-emulsion particles —INCI name: lecithin (and) caprylic/capric triglycerides (and) tocopheryl acetate (and) retinyl palmitate (and) glycerin (and) alcohol (and) water (such as Nano-Lipobelle A/E reportedly containing 3% each of phospholipid and triglyceride; 1.5% tocopheryl acetate; 0.5% retinyl palmitate; 5% glycerin; 10% ethanol; with the remainder water, and having a reported particle size in the range of 30 to 90 nanometers).

*Laminaria digitata* (sea tangle) extract —INCI name: glycerin (and) water (and) *Laminaria digitata* extract (such as Actiphyte of Sea Tangle GL).

*Macrocystis pyrifera* (sea kelp) extract —INC name: glycerin (and) water (and) *Macrocystis pyrifera* extract (such as Actiphyte of Sea Kelp GL).

*Hippophae rhamnoides* (sea buckthorn) extract —INCI name: glycerin (and) water (and) *Hippophae rhamnoides* extract (such as Actiphyte of Sea Buckthorn GL).

*Crithmum maritimum* (sea fennel) extract —INCI name: glycerin (and) water (and) *Crithmum maritimum* extract (such as Actiphyte of Sea Fennel GL).

Algae Extract —INCI name: glycerin (and) water (and) algae extract (such as Actiphyte of Algae).

Acrylates copolymer —INCI name for linear copolymers of acrylic acid sold under the trade name AVALURE® AC 120 by Noveon, Inc.

Broad and specific examples of preferred embodiments of skin care compositions are illustrated in Table 1. The actives % content of an ingredient, where indicated, refers to the reported solids content (i.e., non-water content) of the material as supplied.

TABLE 1

| | PARTS BY WEIGHT | |
|---|---|---|
| INGREDIENTS (INCI/Common Name) | Broad Example A | Specific Example B |
| 1. Glycerin | 2-10 | 6 |
| 2. Mannitol (75%) | 0.5-4.5 | 3.5 |
| 3. Sorbitol (70%) | 0.5-4 | 3 |
| 4. Chelating agent | q.s. | q.s. |
| 5. Cetyl phosphate | 1.75-4.25 | 3 |
| 6. Sodium hydroxide (50% aq.) to pH 6-6.5 | q.s. | q.s. |
| 7. Isodecyl oleate | 5-12 | 8 |
| 8. Cetyl stearate | 0.5-4.5 | 2 |
| 9. Cetearyl alcohol | 2.25-4.75 | 3.5 |
| 10. Dimethicone | 0.1-1 | 0.5 |
| 11. *Aloe barbadensis* leaf juice - 40X | 0.15-2 | 1.4 |
| 12. Product colorant | q.s. | q.s. |
| 13. D, L-Panthenol | 0.05-1 | 0.8 |
| 14. Cyclopentasiloxane | 1.75-9 | 4 |
| 15. Nano-Emulsion particles (8%) | 0.05-5 | 1 |
| 16. *Laminaria digitata* (sea tangle) extract (50%) | 0.5-5 | 1 |
| 17. *Macrocystis pyrifera* (sea kelp) extract (50%) | 0.5-5 | 1 |
| 18. *Hippophae rhamnoides* (sea buckthorn) extract (50%) | 0.5-5 | 1 |
| 19. *Crithmum maritimum* (sea fennel) extract (50%) | 0.5-5 | 1 |
| 20. Algae extract (50%) | 0.5-5 | 1 |
| 21. Sodium hyaluronate (0.5% aq.) | 0.02-4.5 | 3 |
| 22. Preservative | q.s. | q.s. |
| 23. Acrylates copolymer (30%) | 0.05-2 | 0.2 |
| 24. Fragrance | q.s. | q.s. |
| 25. Water, deionized, to 100 parts by weight | q.s. | q.s. | q.s. = quantity sufficient

In the above examples, a preferred method for preparing the skin care emulsion composition comprises the steps of:

1. Preparing a first emulsion phase (A) by:

(i) forming a substantially homogeneous water phase (W) at a temperature maintained in the range of about 70 to about 76° C., preferably in the range of about 72 to about 74° C., comprising water (Ingredient No. 25) and ingredient nos. 1-5 and then neutralizing ingredient no. 5 in situ by adding ingredient no. 6, to the so formed water phase to a pH in the range of about 6 to about 6.5;

(ii) forming a substantially homogeneous oil phase (O) at a temperature maintained in the range of about 70 to about 76° C., preferably in the range of about 72 to about 74° C., comprising ingredient nos. 7-10;

(iii) adding the oil phase (O) to the water phase (W), while maintaining the temperature of the admixture in the range of about 70 to about 76° C., preferably in the range of about 72 to about 74° C., with mixing until homogeneous, to form an oil-in-water emulsion, and then;

(iv) cooling the formed oil-in-water emulsion of step (iii) gradually to a temperature in the range of about 40 to about 45° C. while adding ingredient nos. 11-14 individually in the order listed, mixing after each addition to substantial homogeneity, preferably adding ingredient nos. 11 and 12 when the temperature is in the range of about 60 to about 65° C., and adding the remaining ingredients when the temperature is in the range of about 44 to about 45° C.; to provide first emulsion phase (A); and then 2. Preparing a second emulsion phase (B) by:

(v) further cooling the first emulsion phase (A) provided in step (1-iv) to a temperature in the range of about 36 to about 40° C., preferably in the range of about 38 to about 39° C., and adding the nano-emulsion ingredient no. 15, and mixing until homogeneous to thereby incorporate the nano-emulsion in the pre-formed first oil-in-water emulsion (A) to provide second emulsion phase (B); and then 3. Preparing a final skin care composition by;

(vi) further cooling the emulsion phase (B) of step (2-v) to a temperature in the range of about 35 to about 39° C., more preferably in the range of about 37 to about 38° C., and adding ingredient nos. 16-24 individually in the order listed, mixing until substantially homogeneous after each addition.

EXAMPLE 2

The embodiment of specific Example 1(B) in Table 1 was prepared by the procedure of Example 1. The composition was in the form of a glossy, opaque cream, had a pH in the range of about 6 to about 6.5 measured at a temperature of about 25° C.; and had a viscosity in the range of about 75,000 to about 125,000 (mPa·s) measured at a temperature of about 25° C., (Brookfield rotating viscometer, Model RVT with helipath, at 5 rpm with spindle No. D-5), after a storage period of about 48 hours. The product remained visibly stable on storage at an elevated temperature of about 50° C. for at least about three months.

EXAMPLE 3

The cream embodiment of Example 2 was topically applied to the skin of the back of the hand, and manually spread over the skin. The cream had good slip and glided easily over the skin. The skin felt smooth to the touch and had a desirable moisturized appearance. After a period of about three to about five minutes, the surface of the skin was wetted with water, and the water beaded on the surface. The result indicated that the skin care composition deposited a water-resistant film or coating on the skin surface.

When the skin care composition was applied to the skin of the face, the skin maintained a moisturized, dewy, appearance that lasted all day, and a firm, uplifting sensation was discerned.

EXAMPLE 4

This example illustrates a composition of Example 1(B) used in conjunction with individual commercial eye shadow cosmetics. Three commercial cosmetic products, A, B, and C, identified below, were evaluated. Two of the commercial cosmetics, A and B, were non-aqueous powders and commercial cosmetic, C, was an aqueous gel-like cream.

Eyeshadow A: Powder eye shadow (hue #8), (Color Lab Cosmetics, IL).

General evaluation method (I): The eyeshadow (A) was a loose powder and was removed from its container using a non-metallic scoop having a dry weight capacity of about 0.05 to about 0.075 grams and a liquid weight capacity of about 0.1-0.15 grams. One scoop of eyeshadow A and one scoop of a composition of Example 1(B) were mixed together with a non-metallic spatula on a flat palette surface. The eye shadow admixture of A/Ex. 1 (B), blended readily, had a creamy consistency and was soft, moist and spreadable on the skin. The applied admixture dried to a non-tacky consistency on the skin. The desired cosmetic colorant effect was judged achieved with a lesser amount of the admixture than with the comparative commercial eyeshadow A.

General evaluation method (II): The composition of Example 1(B) was applied to the eye lid and subsequently immediately thereafter the eyeshadow A was applied with a brush to the same eye lid area. The cosmetic effect achieved with the so applied eyeshadow was vivid, remained uniform and lasted for hours without smearing or collecting in the skin fold area (crease) of the eyelid (i.e., commonly referred to as "creasing"). Additionally, more eye shadow (either as admixture or as the commercial product) was successfully applied over the same skin area to create an illusion of more depth and achieve a uniform, multiple color layering effect. In contrast, the commercial eyeshadow A, by itself, was less effective, initially requiring more eyeshadow to be applied to achieve a visible colorant cosmetic effect and the coloration was less vivid, showed creasing, and did not last, i.e., the visible colorant cosmetic effect diminished, fading over time.

Eye shadow B: RIMMEL LONDON Color Rush trio eyeshadow (Rimmel Inc., NY).

The commercial eyeshadow B was a pressed powder and was evaluated similarly to eyeshadow A, except that the product was removed from its container with a wooden spatula and then scooped for evaluation by method (I). The results using eyeshadow B in conjunction with the composition of Example 1(B) either as an admixture (general evaluation method (I)) or subsequent to application of Example 1(B) (general evaluation method (II)) were also judged superior (i.e., remained uniform, non-smearing, non-creasing) compared to those achieved with the commercial eyeshadow B alone.

Eyeshadow C: WET N WILD® MEGA EYES® Créme Eyeshadow (champagne toast) (Markwins Beauty Products, Inc., CA).

Commercial eyeshadow C was evaluated similarly to eyeshadow A, except that it was applied using a brush and a sponge. The results using eyeshadow C in conjunction with the composition of Example 1(B) were also judged superior (i.e., remained uniform, non-smearing, non-creasing) compared to those achieved with the commercial eyeshadow C alone. Commercial eyeshadow C was too liquid on application, smeared and "creased."

For comparison, similar evaluations were made except that a conventional commercial moisturizer product was used in conjunction with the foregoing commercial eyeshadows, in place of the composition of Example 1(B). The commercial moisturizers evaluated were AVEENO® Active Naturals Positively Radiant Daily Moisturizer (Distributed by Johnson & Johnson Consumer Companies, Inc., NJ), which, according to the product's label, reportedly is oil-free, contains a soy complex and natural light diffuser; NEUTROGENA® Oil-Free MOISTURE for combination skin (Neutrogena Corporation, CA), a creamy emulsion; and L'Oréal® Paris Active Daily Moisture Lotion with Pro-Vitamin B5, for all skin types, (L'Oréal USA, NY) which lists U.S. Pat. No. 4,661,343 on the label. In all cases, the admixture consistency and the cosmetic effects achieved were generally unacceptable.

EXAMPLE 5

This example demonstrates a composition of Example 1(B) used in conjunction with a commercial lipstick (No regrets shade), (Color Lab Cosmetics, IL). In one aspect, a composition of Example 1(B) was applied to the lips with the fingers and substantially immediately thereafter, the lipstick was applied to the lips. In a second aspect, the lipstick was applied to the lips and then substantially immediately thereafter, the composition of Example 1(B) was applied to the lips. In each case, the colorant cosmetic effect on the lips remained vivid, uniform, and long lasting, with no bleeding or caking in the creases of the lips. In comparison, the colorant effect achieved with the commercial lipstick alone applied as described did not last as long, diminishing and fading with time.

In a third aspect, an admixture of the composition of Example 1(B) was prepared by removing the lipstick from its container with a wooden stick and then mixing one scoop of lipstick with one scoop of the composition of Example 1(B). The lipstick admixture was very soft and creamy, and was evenly spreadable on the lips with a lip brush. The lipstick admixture moistened and adhered uniformly to the skin and blended color into the lip, resulting in a longer lasting result than that of the commercial lipstick alone. The commercial lipstick was less creamy, did not spread as easily and tended to adhere less well (coated the surface of the lip).

EXAMPLE 6

This example demonstrates a composition of Example 1(B) used in conjunction with commercial mascara. Three individual commercial mascara products, A, B, and C, identified below were evaluated. Two of the mascaras, A and B, were wand-in-tube mascaras that list water among the ingredients, and the other mascara, C, was a non-aqueous cake mascara.

Mascara A: VOLUME Mascara (#04 violet), (Yves Saint Laurent, FR). This commercial mascara product is usually applied to the lashes with the mascara-coated wand and dries very quickly. In one aspect, a composition of Example 1(B) was applied to the eye lashes with a cotton tipped application and substantially immediately thereafter, the mascara was applied to the eye lashes. The colorant effect (violet) was surprisingly enhanced, the lashes were longer looking and hydrated.

In another aspect, a scoopful of the composition of Example 1(B) was placed on a stainless steel mixing palette and the commercial mascara was admixed therein by rolling the mascara-coated wand through the Example 1(B) cream. The mascara admixture adhering to the wand was then applied to the eyelashes. The colorant effect produced was surprisingly vibrant and the admixture had better spreadability in applying it to eye lashes, than the commercial mascara A alone. The color was more dispersed throughout the lashes and more product was visible. The mascara admixture remained moist and did not dry out in seconds as did the commercial product, leaving the lashes soft and touchable without smearing or flaking. The lashes retained a moist wet appearance after application so additional mascara could be applied for multiple use.

Mascara B: MAYBELLINE Great Lash (Black) (Maybelline, NY). This commercial mascara is usually applied to the lashes with the mascara-coated wand and has a tendency to clump on the lashes. The product was evaluated in a manner similar to the one described for commercial mascara A and the colorant results were again judged superior to those achieved with the commercial product alone.

Mascara C: PAULA DORF Cake Mascara (Paula Dorf Cosmetics, NY). This commercial mascara is usually applied to the lashes with a brush moistened with water. The product was evaluated in a manner similar to the one described for commercial mascara A, except that the product was applied to the lashes with a brush. The colorant results were again judged superior to those achieved with the commercial product alone.

EXAMPLE 7

This example demonstrates a composition of Example 1(B) used in conjunction with commercial facial powder, PIAFFE pressed powder (cream shade), (Manufactured by Your Name Cosmetics for Piaffe Cosmetics, NY). The powder was scraped from the container and a scoopful of the powder was admixed with a scoopful of the composition Example 1(B). The facial powder admixture had a creamy, lotion-like consistency, was soft and spreadable over the skin like a lotion and had the coverage of a cream foundation makeup. The finished effect was a soft, natural, matte appearance and the skin felt hydrated. Surprisingly, multiple applications of the admixture provided a layering technique for achieving both a cosmetic cover up and concealer effect, which would beneficially eliminate the need for using multiple pigmented products. The result obtained with the admixture was judged superior to that obtained with the commercial product alone.

EXAMPLE 8

This example demonstrates the versatility of using a composition of Example 1(B) in conjunction with various types of commercial pigmented makeup. Eight commercial products, A-H, identified below were separately evaluated by mixing together equal parts (i.e., one scoop of each) of the commercial makeup and the composition of Example 1(B) and applying the admixture to the skin.

Makeup A: PIAFFE Mineral Sheer Tint liquid foundation (light)(Manufactured by Your Name Cosmetics for Piaffe Cosmetics, New York, N.Y.). This cosmetic is reportedly oil and fragrance free with a hint of color, contains sunscreen and vitamins A, C and E. The admixture spread over the skin more readily than did the commercial tint foundation alone, and no flaking or smearing of the pigment on the skin was observed. The skin had a moist, youthful glowing appearance, and the applied color remained consistent through the day (i.e., the visible color applied did not change tone or "fade". The commercial foundation alone tends to disappear and be absorbed by the skin and the oils present on the skin tend to discolor the colorant to produce an unaesthetic orange/yellow cast on the skin.

In a comparative evaluation using admixtures of commercial moisturizers described in Example 4, in place of the compositions of Example 1(B), results were unsatisfactory. The texture of the admixture was either rubbery or too greasy indicating incompatibility between the moisturizers and the foundation, and the colorant effect on the skin did not last.

Admixtures of the composition of Example 1(B) with each of the following commercial makeup products listed below also produced results that were judged superior compared to that achieved with the commercial makeup product alone.

Makeup B: ALMAY NEARLY NAKED® Touch-Pad Liquid Makeup (Almay, Inc. Dist., NY). According to the label, this makeup is anhydrous (no water among the listed ingredients), is reportedly oil-free with Vitamins A and E and grape seed, and lists U.S. Pat. Nos. 4,578,266; 6,464,964; and 6,780,422.

Makeup C: BE PURE Mineral Makeup powder (01 colorless) (Jane &Co., Inc, NY). According to the label, this powder product is talc free. The product is reportedly oil free, wax free and fragrance free.

Makeup D: L'ORÈAL PARIS Super Blendable Makeup (Neutral) Liquid (L'Orèal USA, Inc.). According to the label, this liquid makeup contains water and must be shaken well before using.

Makeup E: SALLY HANSEN® ANTI-AGING AIRBRUSH Makeup (Nude Tan) (Sally Hansen Div., Dist. Del Laboratories, Inc. NY). This product lists water among the ingredients and is an aerosolized product. For use the product is normally expelled from the container onto the fingers and applied to the skin with the fingers. The application of the product alone was judged to be unaesthetic, and was vastly improved by admixing with the composition of Example 1(B).

Makeup F: RIMMEL Cool Matte 16 Hr Mousse Foundation (#200 soft beige) (Rimmel Inc., NY).

Makeup G: COVER GIRL® CG Smoothers SPF 15 Moisture (light to medium tint) (Procter & Gamble Distr. CA). According to the label, the product contains water among the listed ingredients, contains moisturizers and Vitamin E, a broad spectrum sunscreen, and is reportedly oil-free, PABA free and fragrance free.

Makeup H: MAYBELLINE Dream Mousse Blush (#20 peach satin) (Maybelline LLC, NY). According to the label, the product is anhydrous (no water among the listed ingredients). The admixture of this product with the composition of Example 1(B) was also judged suitable for use as a lip product.

The foregoing examples illustrate the versatility and efficacy of the skin care composition of this invention in augmenting, and maintaining a desired cosmetic colorant effect on the skin when used in conjunction with a pigmented cosmetic. The examples illustrate the use of the skin care composition applied before, during and/or after an application of a pigmented cosmetic. Thus, a powder cosmetic can be used as a cream, a blush can be used as a lip colorant, an eye product can be used as an eyeshadow or as an eye liner, and the like. This versatility provides the user with the benefits of multipurpose cosmetics without the cost associated with purchasing separate cosmetics.

The present invention has been described generally and with respect to preferred embodiments. It will be understood that modifications and variation of the disclosed composition may be made without departing from the spirit and scope of the novel concept of the present invention.

What is claimed is:

1. An aqueous topical, cosmetic skin care composition consisting essentially of the following components
    (a) an effective skin-moisturizing amount of an oil-in-water nano-emulsion comprising phospholipid-stabilized submicron triglyceride particles having a unimolecular shell of phospholipid having a phosphatidylcholine stabilizer to encapsulate an oil core comprising triglyceride and auxiliary lipophilic skin conditioning agents, water, and cosmetically acceptable water-soluble solvents selected from the group consisting of alcohol, liquid polyol and a combination thereof, the amount of oil-in-water nano-emulsion being about 0.005 to 5 parts by weight based on a total weight of the cosmetic skin care composition;
    (b) an effective skin-conditioning amount of a botanical material provided in its own individual hydroglycolic vehicle, the botanical material being selected from the group consisting of a vegetal material, a marine material, and a combination thereof, the amount of botanical material being about 0.25 to 10 parts by weight based on a total weight of the cosmetic skin care composition, the individual hydroglycolic vehicle having a pH of about pH4 to PH7;
    (c) a polycarboxylate polymer selected from the group consisting of a copolymer of two or more monomers of acrylic acid, methacrylic acid or one of their simple esters, the polycarboxylate polymer being present in the cosmetic skin care composition in an amount of 0.1 to 2 parts by weight based on a total weight of the cosmetic skin care composition;
    (d) an effective emulsifying amount of a phosphate ester-type emulsifier selected from the group consisting of a $C_8$-$C_{22}$ fatty alcohol phosphate diester, and a salt of the foregoing, the phosphate ester-type emulsifier comprising about 2 to about 20 moles of alkoxylating moieties for each fatty alcohol moiety, the amount of phosphate ester-type emulsifier being about 1 to 5 parts by weight based on a total weight of the cosmetic skin care composition;
    (e) a cosmetically acceptable auxiliary skin conditioning agent, the conditioning agent being present in the cosmetic skin care composition in an amount equal to or greater than 10 parts by weight based on a total weight of the cosmetic skin are composition; and
    (f) water;
    wherein the composition is an opaque emulsion in the form of a lotion or substantially semi-solid cream or paste,
    wherein the composition is a leave-on cosmetic preparation, which, on topical application to the skin, provides a lasting, water-resistant, moisturizing, conditioning film or coating thereon,
    wherein the composition has a pH of about pH 6 to pH 6.5,
    wherein the composition has a viscosity of about 50,000 to 150,000 (mPa*s) measured at temperature of about 25° C., and wherein the cosmetically acceptable auxiliary skin conditioning agent includes a combination of isodecyl oleate, dimethicone and cyclopentasiloxane.

2. The composition of claim 1 wherein the phospholipid in component (a) is selected from the group consisting of naturally derived lecithin and a synthetically prepared lecithin derivative.

3. The composition of claim 1 wherein the triglyceride in component (a) is selected from the group consisting of glyceryl $C_6$-$C_{22}$ fatty acid mono-ester, glyceryl $C_6$-$C_{22}$ fatty acid di-ester, glyceryl $C_6$-$C_{22}$ fatty acid tri-ester, and a combination thereof.

4. The composition of claim 1 wherein the triglyceride in component (a) is a caprylic/capric triglyceride.

5. The composition of claim 1 wherein the botanical material comprises a *Hippophae rhamnoides* (sea buckthorn) extract.

6. The composition of claim 1 wherein the botanical material comprises a *Laminaria digitata* (sea tangle) extract.

7. The composition of claim 1 wherein the botanical material comprises a *Macrocystis pyrifera* (sea kelp) extract.

8. The composition of claim 1 wherein the botanical material comprises a *Crithmum maritimum* (sea fennel) extract.

9. The composition of claim 1 wherein the botanical material comprises an algae extract.

10. The composition of claim 1 wherein the botanical material comprises an Aloe.

11. The composition of claim 10 wherein the Aloe comprises an *Aloe barbadensis* gel.

12. The composition of claim 1 wherein the polycarboxylate polymer is a linear copolymer of acrylic acid.

13. The composition of claim 1 wherein the composition is admixed by a user of the composition with a separately prepared substantially anhydrous skin-colorant composition to create a cosmetic composition combination, and wherein the substantially anhydrous skin-colorant composition is in the form of a liquid, paste, powder or stick.

14. A composition of claim 1 in packaged form.

15. An article of manufacture comprising a cosmetic kit containing, in separately packaged form, (A) the composition of claim 14, (B) at least one colorant cosmetic skin-care composition and (C) instructional indicia for using the compositions of (A) and (B) in conjunction with one another in a skin-beautifying procedure.

16. The article of manufacture of claim 15 wherein component (B) is a substantially anhydrous makeup composition in liquid, paste, powder, or stick form.

17. A method of enhancing, augmenting and maintaining a desired visible cosmetic colorant effect on the skin in a skin-beautifying regime employing a separately prepared pigmented, skin-colorant cosmetic formulated for effecting a predetermined desired visual skin-colorant effect, the method comprising topically applying a composition of claim 1 to the skin-colorant cosmetic either before or after applying the skin-colorant cosmetic to the skin; wherein the resulting visible skin-colorant effect achieved is lasting, enhanced, and/or augmented relative to the effect achieved with the skin colorant cosmetic alone.

18. The composition of claim 1, the composition being a vehicle for a cosmetic product predetermined for adding color to a first skin location to be used on a second skin location once the cosmetic product is admixed with the composition.

19. The composition of claim 1, wherein the alkoxylating moieties are selected from the group consisting of polyethoxylating moieties, polypropoxylating moieties, and a combination of the foregoing.

* * * * *